US009901509B2

(12) United States Patent
Abramovitz

(10) Patent No.: US 9,901,509 B2
(45) Date of Patent: Feb. 27, 2018

(54) EROTIC STIMULATOR DEVICE

(71) Applicant: David Abramovitz, Charlotte, NC (US)

(72) Inventor: David Abramovitz, Charlotte, NC (US)

( * ) Notice: Subject to any disclaimer, the term of this patent is extended or adjusted under 35 U.S.C. 154(b) by 273 days.

(21) Appl. No.: 14/940,782

(22) Filed: Nov. 13, 2015

(65) Prior Publication Data

US 2016/0136035 A1 May 19, 2016

Related U.S. Application Data

(60) Provisional application No. 62/081,070, filed on Nov. 18, 2014.

(51) Int. Cl.
*A61F 5/00* (2006.01)
*A61H 19/00* (2006.01)

(52) U.S. Cl.
CPC ..... *A61H 19/32* (2013.01); *A61H 2201/0153* (2013.01); *A61H 2201/0207* (2013.01); *A61H 2201/0257* (2013.01); *A61H 2201/1253* (2013.01); *A61H 2201/1654* (2013.01); *A61H 2201/1688* (2013.01)

(58) Field of Classification Search
CPC ......... A61H 19/30; A61H 19/32; A61H 19/50
USPC ........................................................ 600/38–41
See application file for complete search history.

(56) References Cited

U.S. PATENT DOCUMENTS

| | | | | |
|---|---|---|---|---|
| 5,622,186 A * | 4/1997 | Schwartz | A61F 5/41 | 128/842 |
| 6,149,580 A * | 11/2000 | Dabney | A61H 19/00 | 600/38 |
| 2006/0264856 A1* | 11/2006 | Wong | A61H 19/00 | 604/349 |

* cited by examiner

*Primary Examiner* — John Lacyk
(74) *Attorney, Agent, or Firm* — Blake E. Vande Garde; Erickson Kernell IP, LLC

(57) ABSTRACT

An erotic stimulator device comprising a mat including an inner surface and an outer surface, a hook and loop fastening system wherein a hook portion of the system is secured to one mat surface and a loop portion of the system is secured to the opposite mat surface and a sleeve having an open end and a closed end wherein the sleeve is placed on the inner surface of the mat with the open end of the sleeve extending outside the perimeter of the sleeve, the mat is rolled up into a cylindrical shape with the sleeve inside and the hook and loop fastening system is engaged to maintain the shape of the mat and the open end of the sleeve is extended from the inner surface to the outer surface of the mat.

20 Claims, 3 Drawing Sheets

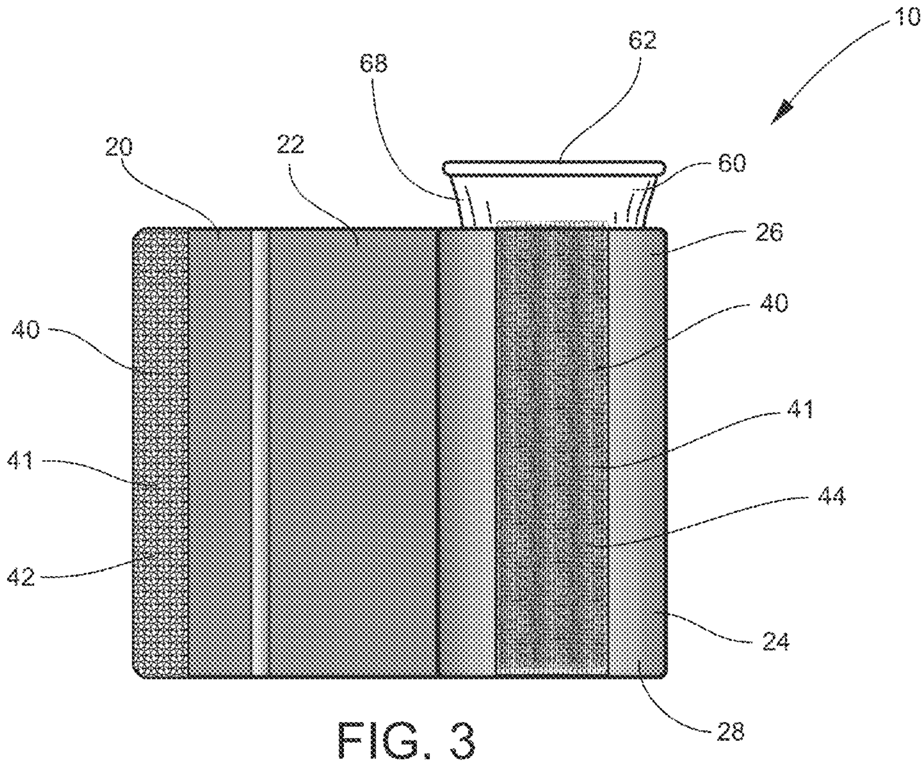
FIG. 3
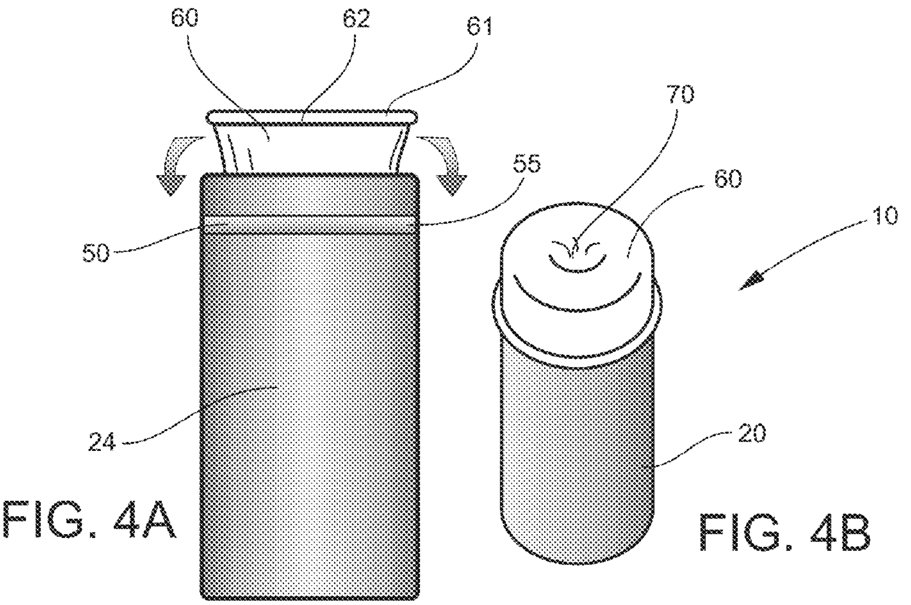
FIG. 4A
FIG. 4B

EROTIC STIMULATOR DEVICE

RELATED CASES

This application claims the priority of provisional application Ser. No. 62/081,070 filed Nov. 18, 2014. Applicant hereby incorporates by reference the entire content of provisional application Ser. No. 62/081,070.

FIELD OF THE INVENTION

The present invention relates to sexual aid devices and more specifically to a device and method for facilitating a male orgasm.

BACKGROUND OF THE INVENTION

The sexual stimulation of a person's genitals by that person for their own pleasure may be as old as human kind. There are depictions of male and female masturbation in prehistoric rock paintings in various locations around the world. Depictions of masturbation in the ancient world are common. Devices used by males to aid in masturbation have likely existed for centuries. In the twentieth and twenty-first centuries, the number of masturbation aid devices has increased dramatically. The early 1900's saw the inflatable "blow-up" doll introduced. The late 1900's saw the introduction of the more discreet Fleshlight™. The twenty-first century has introduced a whole new line of devices which, with the aid of computer technology can interact with videos and even other devices. Unfortunately, the latest devices can be cost prohibitive for many potential users. Hence, it is clear that a need exists to provide a simple, inexpensive device and method for facilitating a male orgasm.

SUMMARY OF THE INVENTION

An erotic stimulator device comprising a mat including an inner surface and an outer surface, a fastening system secured to the mat surface and a sleeve having an open end and a closed end wherein the sleeve is placed on the inner surface of the mat with the open end of the sleeve extending outside the perimeter of the sleeve, the mat is rolled up into a cylindrical shape with the sleeve inside and the hook and loop fastening system is engaged to maintain the shape of the mat and the open end of the sleeve is extended from the inner surface to the outer surface of the mat.

DESCRIPTION OF THE DRAWINGS

For the purpose of illustrating the invention, there is shown in the drawings a form that is presently preferred; it being understood, however, that this invention is not limited to the precise arrangements and instrumentalities shown.

FIG. 3 is a side view of one embodiment of the present invention in partially rolled configuration.

FIG. 4A is a side view of a sleeve being configured on one embodiment of the present invention.

FIG. 4B is a proximal view of one embodiment of the present invention.

DETAILED DESCRIPTION

Figure 1A:
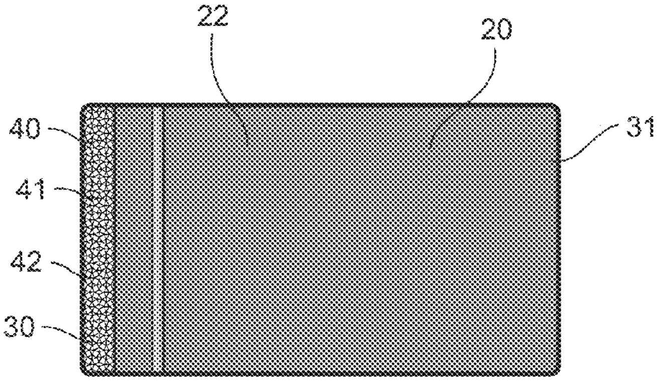
FIG. 1A is a side view of one embodiment of the present invention in a flat, unrolled configuration.

The present invention now will be described more fully hereinafter in the following detailed description of the invention, in which some, but not all embodiments of the invention are described. Indeed, this invention may be embodied in many different forms and should not be construed as limited to the embodiments set forth herein; rather, these embodiments are provided so that this disclosure will satisfy applicable legal requirements.

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

Looking now to the figures where like numbers indicate like items, there is illustrated several embodiments of an erotic stimulator device 10 comprising a mat 20 which has an inner surface 22 and an outer surface 24. The mat 20 is designed to be ergonomic for manual use to provide grip and pleasurable sensation to assist with male masturbation and ejaculation. The mat 20 also has a proximal end 26, a distal end 28, a first edge 30 and a second edge 31. The mat 20 may be any shape which allows the mat to be rolled into a cylindrical shape. In one embodiment, the mat 20 is square or rectangular. In another embodiment, the mat 20 is flat. In one embodiment, the mat 20 is made of natural fibers, natural yarns, natural threads, man-made fibers, man-made yarns, man-made threads, or a combination thereof. In another embodiment, the mat 20 is made of cotton, polyester, or a combination thereof. In still another embodiment, the mat is washable. In one embodiment, the mat 20 is made from textiles, not like your normal masturbation aids which are made of plastic, rubber and/or silicone. In another embodiment the mat 20 is made of plastic, rubber and/or silicone. In still another embodiment, the mat 20 is made of a combination of textiles, plastic, rubber and/or silicone. The mat 20 may be hollow and contain one or more types of a padding within the mat. The hollow mat 20 may include a closing mechanism, such as those listed below as part of the fastening system 40 to gain or restrict access to the hollow portion within the mat. The padding can be made of natural fibers, man-made fibers, or a combination thereof. The padding may be washable or disposable. The padding may be warmed and retain heat prior to, during and after use.

A fastening system 40 is secured to the mats surface 22, 24. The fastening system 40 used to retain the mat in a cylindrical shape may include any fastening system known in the art. These systems include hook-and-eye closures (such as those used on bras), snaps, buttons, elastic bands, strings, laces (for tying), zippers, adhesives, magnets, or any combination thereof. In one embodiment of the instant invention, a hook and loop fastening system 41 is used and located on the surfaces 22, 24 of the mat 20. In one embodiment, the hook portion 42 of the fastening system 40 is located on one surface (i.e. the inner surface 22) and the loop portion 44 of the fastening system is located on the opposite surface (i.e. the outer surface 24) or vice versa. In another embodiment, both the hook portion 42 and the loop portion 44 of the fastening system 40 are located on the same surface. In the embodiment illustrated in the Figures, one portion of the fastening system (i.e. 42) is located on the first edge 30 of the mat which is located on the inner surface 22 of the mat and the other portion of the fastening system (i.e. 44) is located on the outer surface 24 of the mat.

The erotic stimulator device 10 also includes a sleeve 60 which may be considered a collection device. The sleeve 60 includes a ridge 61 located at the open end 62 of the sleeve with a closed end 64 located opposite the open end. The sleeve 60 also has an inner surface 66 and an outer surface 68. The sleeve 60 is a compliant material with one open end and comprised of a material which will provide a pleasurable sensation to assist with masturbation and ejaculation. The sleeve 60 can be made out of any material, natural or synthetic, which is known and accepted within the industry, for use in male stimulation/masturbation devices. The sleeve 60 can be made of natural material, man-made material, or a combination thereof. In one embodiment, the sleeve 60 is made of natural latex, synthetic latex, natural rubber, synthetic rubber, silicone, elastomer, thermal plastic elastomer, thermoplastic rubber, plastic, or a combination thereof. The sleeve 60 can also be reusable, washable, disposable, or a combination thereof.

In one embodiment, the mat 20 could be likened to an outer shell and the sleeve 60 could be likened to an inner shell. The mat 20 has various attachment points or mechanisms (fastening system 40) to provide for a secure closure as well as to provide a method by which to attach or secure the sleeve 60 while the device is being operated. In one embodiment, the erotic stimulator device also includes a sleeve guide ridge 50, a sleeve guide slot 55, or a combination thereof, located on the outer surface 24 of the mat 20 wherein the open end 62 of the sleeve 60 is placed or secured near the ridge 50 or slot 55. The mat 20 must have one end open (the proximal end 26) for insertion of the penis into the sleeve when fully assembled. The sleeve 60 is placed inside the mat 20 against the mat's inner surface 22 with the open ends (26 and 62) aligned for insertion of the penis. The mat 20 is then sealed to provide a snug and comfortable chamber which will retain the sleeve 60 and allow the penis to be inserted into the opening 70. Put another way, the sleeve 60 is an insert that acts as a lining for the interior of the device 10. This lining is the surface a user's penis will be in contact with during use. The sleeve 60 also catches the semen after orgasm. In one embodiment, the tightness of the mat 20 when rolled into a cylindrical shape is adjustable to a user's preference.

Figure 1B:
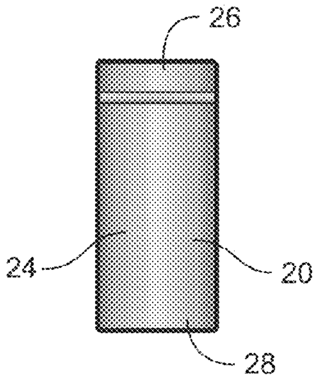
FIG. 1B is a side view of one embodiment of the present invention in a rolled configuration.
Figure 2:
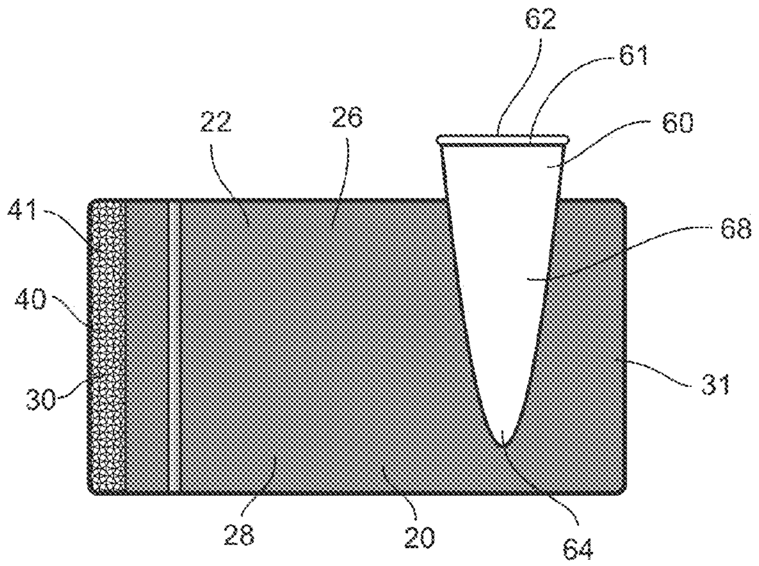
FIG. 2 is a side view of one embodiment of the present invention in a flat, unrolled configuration.
Figure 5:
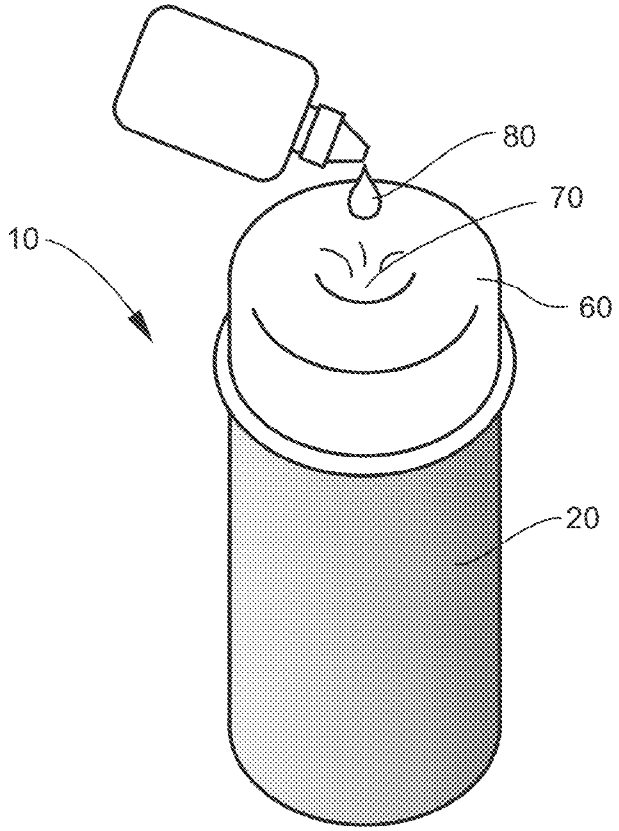
FIG. 5 is a proximal view of one embodiment of the present invention.
Figure 6:
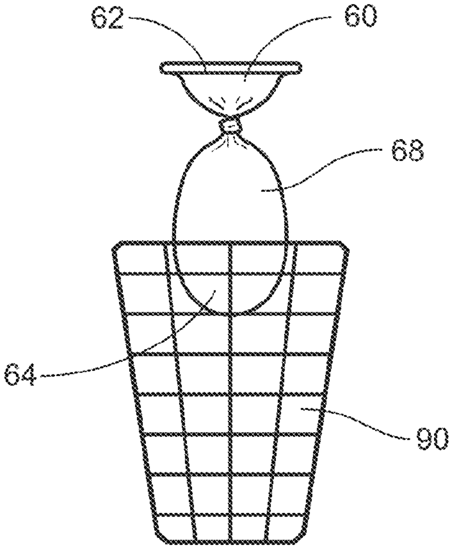
FIG. 6 is a side view of the disposal of a sleeve of one embodiment of the present invention.

One embodiment of the erotic stimulator device 10 is a masturbation device for men. The mat 20 made out of soft material (60% Polyester, 40% cotton blend), hook and loop fastening system 41, and a 100% Polyester filling within the mat 20. The mat 20 may be made of natural fibers, natural yarns, natural threads, man-made fibers, man-made yarns, man-made threads, or a combination thereof. The mat 20 may also include spandex, cotton, muslin, foam, nylon, rope, string, cording, hook and loop fasteners, or a combination thereof. The device 10 is designed to be opened and lay flat (FIGS. 1A and 1B). Once laid flat, a sleeve 60 lays flat near the proximal end 26 of the device with the open end 62 laying 2 to 3 inches outside of the device (FIG. 2). The sleeve 60 is rolled up within the device (FIG. 3) until the hoop and loop fastening system 41 adheres shut and creates a cylindrical shape similar to the size of a can of tennis balls (FIGS. 4 and 5). The excess open end 62 of the sleeve 60 gets pulled down over the device (FIG. 4) and lubricant 80 is added (FIG. 5). The ridge 61 located on the open end 62 of the sleeve is hooked over a sleeve guide ridge 50 or placed within a sleeve guide slot 55 in order to hold the sleeve 60 in place while in use. The result is a tight hole (opening 70) that can be used for masturbation. On completion, the user can remove the sleeve 60 and dispose of the sleeve in a trash receptacle 90 (FIG. 6).

Another embodiment of the instant invention discloses an erotic stimulator device 10 comprising a mat 20 including an inner surface 22 and an outer surface 24, a hook and loop fastening system 41 wherein a hook portion 42 of the system is secured to one mat surface and a loop portion 44 of the system is secured to the opposite mat surface and a sleeve 60 having an open end 62 and a closed end 64. The sleeve 60 is placed on the inner surface 22 of the mat with the open end 62 of the sleeve extending outside a perimeter of the sleeve. The mat 20 is rolled up into a cylindrical shape with the sleeve 60 inside and the hook and loop fastening system 41 is engaged to maintain the shape of the mat 20 and the open end 62 of the sleeve is extended from the inner surface 22 to the outer surface 24 of the mat forming an opening 70 into the sleeve which extends within the inner surface of the cylindrically shaped mat 20. One or more kinds of lubricant 80 are deposited into the opening 70 at the open end 62 of the sleeve 60 and onto the inner surface 66 of the sleeve. The tightness of the mat 20 when rolled into a cylindrical shape is adjustable to a user's preference by adjusting the hook and loop fastening system 41. The above embodiment may further comprise a sleeve guide ridge 50, a sleeve guide slot 55, or a combination thereof, wherein the open end of the sleeve 60 is placed or secured within or near the ridge 50 or slot 55.

The instant invention also includes a process for facilitating a male orgasm comprising the steps of:

a. providing an erotic stimulator device 10 comprising a mat 20 including an inner surface 22 and an outer surface 24, a fastening system 40 secured to the mat surface and a sleeve 60 having an open end 62, a closed end 64, an inner surface 66 and an outer surface 68 wherein the sleeve 60 is placed on the inner surface 66 of the mat with the open end 62 of the sleeve extending outside a perimeter of the sleeve;

b. rolling the mat 20 into a cylindrical shape with the sleeve 60 inside and the fastening system 40 is engaged to maintain the shape of the mat 20; and c. extending the open end 62 of the sleeve 60 from the inner surface 66 to the outer surface 68 of the mat forming an opening 70 into the sleeve which extends within the inner surface 22 of the cylindrically shaped mat 20;

d. applying a lubricant 80 to the opening 70 into the sleeve 60;

e. inserting a male's penis into the opening 70 into the sleeve;

f. gripping the outer surface 24 of the mat 20, and g. moving the device 10 up and down the shaft to stimulate the penis and facilitate the male to an orgasm.

The above process may further comprise the steps of:

h. retracting the sleeve 60 from the outer surface 24 of the mat 20;

i. removing the sleeve 60 from the interior of the cylindrically shaped mat 20;

and j. disposing of the sleeve 60.

In one embodiment, the above process further comprises a sleeve guide ridge 50, a sleeve guide slot 55, or a combination thereof, wherein the open end 62 of the sleeve 60 is placed or secured within or near the ridge 50 or slot 55. In another embodiment, the above fastening system 40 is a hook and loop fastening system 41 wherein a hook portion 42 of the system is secured to one mat surface and a loop portion 44 of the system is secured to the opposite mat surface. In still another embodiment, the mat 20 is hollow and contains one or more types of a padding within the mat. In yet another embodiment, the sleeve 60 is made of natural material, man-made material, or a combination thereof. The sleeve 60 is made of natural latex, synthetic latex, natural rubber, synthetic rubber, silicone, elastomer, thermal plastic elastomer, thermoplastic rubber, plastic, or a combination thereof. The sleeve is reusable, washable, disposable, or a combination thereof.

Any method described herein may incorporate any design element contained within this application and any other document/application incorporated by reference herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims. The present invention may be embodied in other forms without departing from the spirit and the essential attributes thereof, and, accordingly, reference should be made to the appended claims, rather than to the foregoing specification, as indicating the scope of the invention. The invention illustratively discloses herein suitably may be practiced in the absence of any element which is not specifically disclosed herein.

What is claimed is:

1. An erotic stimulator device comprising:
a mat including an inner surface and an outer surface;
a fastening system secured to the mat surface; and
a sleeve having an open end and a closed end;
wherein the sleeve is placed on the inner surface of the mat with the open end of the sleeve extending outside a perimeter of the sleeve;
wherein the mat is rolled up into a cylindrical shape with the sleeve inside and the fastening system is engaged to maintain the shape of the mat; and
wherein the open end of the sleeve is extended from the inner surface to the outer surface of the mat forming an opening into the sleeve which extends within the inner surface of the cylindrically shaped mat.

2. The erotic stimulator device of claim 1 further comprising one or more kinds of lubricant.

3. The erotic stimulator device of claim 1 further comprising a sleeve guide ridge, a sleeve guide slot, or a combination thereof, wherein the open end of the sleeve is placed or secured near the ridge or slot.

4. The erotic stimulator device of claim 1 wherein the fastening system is a hook and loop fastening system wherein a hook portion of the system is secured to one mat surface and a loop portion of the system is secured to the opposite mat surface.

5. The erotic stimulator device of claim 1 wherein the mat is hollow and contains one or more types of a padding within the mat.

6. The erotic stimulator device of claim 1 wherein the sleeve is made of natural material, man-made material, or a combination thereof.

7. The erotic stimulator device of claim 6 wherein the sleeve is made of natural latex, synthetic latex, natural rubber, synthetic rubber, silicone, elastomer, thermal plastic elastomer, thermoplastic rubber, plastic, or a combination thereof.

8. The erotic stimulator device of claim 1 wherein the sleeve is reusable, washable, disposable, or a combination thereof.

9. A process for facilitating a male orgasm comprising the steps of:
providing an erotic stimulator device comprising:
a mat including an inner surface and an outer surface;
a fastening system secured to the mat surface; and
a sleeve having an open end and a closed end;
placing the sleeve on the inner surface of the mat with the open end of the sleeve extending outside a perimeter of the sleeve;
rolling the mat up into a cylindrical shape with the sleeve inside and the fastening system is engaged to maintain the shape of the mat;
extending the open end of the sleeve from the inner surface to the outer surface of the mat forming an opening into the sleeve which extends within the inner surface of the cylindrically shaped mat;
applying a lubricant to the opening into the sleeve;
inserting a male's penis into the opening into the sleeve;
gripping the outer surface of the mat; and
moving the device up and down the shaft to stimulate the penis and facilitate the male to an orgasm.

10. The process of claim 9 further comprising a sleeve guide ridge, a sleeve guide slot, or a combination thereof, wherein the open end of the sleeve is placed or secured near the ridge or slot.

11. The process of claim 9 wherein the fastening system is a hook and loop fastening system wherein a hook portion of the system is secured to one mat surface and a loop portion of the system is secured to the opposite mat surface.

12. The process of claim 9 wherein the mat is hollow and contains one or more types of a padding within the mat.

13. The process of claim 9 wherein the sleeve is made of natural material, man-made material, or a combination thereof.

14. The process of claim 13 wherein the sleeve is made of natural latex, synthetic latex, natural rubber, synthetic rubber, silicone, elastomer, thermal plastic elastomer, thermoplastic rubber, plastic, or a combination thereof.

15. The process of claim 9 wherein the sleeve is reusable, washable, disposable, or a combination thereof.

16. The process of claim 9 further comprising the steps of:

retracting the sleeve from the outer surface of the mat;

removing the sleeve from the interior of the cylindrically shaped mat; and disposing of the sleeve.

17. An erotic stimulator device comprising:

a mat including an inner surface and an outer surface;

a hook and loop fastening system wherein a hook portion of the system is secured to one mat surface and a loop portion of the system is secured to the opposite mat surface; and a sleeve having an open end and a closed end;

wherein the sleeve is placed on the inner surface of the mat with the open end of the sleeve extending outside a perimeter of the sleeve;

wherein the mat is rolled up into a cylindrical shape with the sleeve inside and the hook and loop fastening system is engaged to maintain the shape of the mat; and wherein the open end of the sleeve is extended from the inner surface to the outer surface of the mat forming an opening into the sleeve which extends within the inner surface of the cylindrically shaped mat;

one or more kinds of lubricant deposited into the open end of the sleeve and onto the inner surface of the sleeve;

wherein the tightness of the mat when rolled into a cylindrical shape is adjustable to a user's preference.

18. The erotic stimulator device of claim 17 further comprising a sleeve guide ridge, a sleeve guide slot, or a combination thereof, wherein the open end of the sleeve is placed or secured near the ridge or slot.

19. The erotic stimulator device of claim 17 wherein the mat is washable, hollow and contains one or more types of a padding within the mat.

20. The erotic stimulator device of claim 17 wherein the sleeve is made of natural latex, synthetic latex, natural rubber, synthetic rubber, silicone, elastomer, thermal plastic elastomer, thermoplastic rubber, plastic, or a combination thereof.

* * * * *